(12) United States Patent
Viswanath et al.

(10) Patent No.: US 9,023,776 B2
(45) Date of Patent: May 5, 2015

(54) RINSE-OFF COMPOSITIONS COMPRISING LACTOYL ETHANOLAMINE AND A MENTHANECARBOXAMIDE COMPOUND

(75) Inventors: Arun Kumar Viswanath, Singapore (SG); Shreedhar Iyer, Singapore (SG); Paolo Facino, Singapore (SG); Ai Teng Koh, Singapore (SG)

(73) Assignee: Givaudan S.A., Vernier (CH)

( * ) Notice: Subject to any disclaimer, the term of this patent is extended or adjusted under 35 U.S.C. 154(b) by 0 days.

(21) Appl. No.: 14/233,201

(22) PCT Filed: Jul. 26, 2012

(86) PCT No.: PCT/EP2012/064697
§ 371 (c)(1),
(2), (4) Date: Apr. 11, 2014

(87) PCT Pub. No.: WO2013/014235
PCT Pub. Date: Jan. 31, 2013

(65) Prior Publication Data
US 2014/0221265 A1   Aug. 7, 2014

(30) Foreign Application Priority Data

Jul. 26, 2011 (GB) .................................. 1112787.5
May 31, 2012 (GB) .................................. 1209657.4

(51) Int. Cl.
| | |
|---|---|
| C11D 3/50 | (2006.01) |
| A61K 8/34 | (2006.01) |
| A61K 8/42 | (2006.01) |
| A61K 8/49 | (2006.01) |
| A61Q 5/02 | (2006.01) |
| A61Q 19/10 | (2006.01) |

(52) U.S. Cl.
CPC . *A61K 8/347* (2013.01); *A61K 8/42* (2013.01); *A61K 8/4926* (2013.01); *A61Q 5/02* (2013.01); *A61Q 19/10* (2013.01); *A61K 2800/244* (2013.01)

(58) Field of Classification Search
USPC ......... 510/101, 119, 126, 130, 136, 360, 499, 510/501
See application file for complete search history.

(56) References Cited

U.S. PATENT DOCUMENTS 7,001,594 B1   2/2006  Peffly et al.
2010/0292294 A1* 11/2010 Watson et al. ................ 514/423

FOREIGN PATENT DOCUMENTS

| WO | 2005049553 | * | 6/2005 |
| WO | WO 2005/049553 A1 | | 6/2005 |
| WO | WO 2007/019719 A1 | | 2/2007 |
| WO | WO 2008/107137 A2 | | 9/2008 |

OTHER PUBLICATIONS

GB 1112787.5—Great Britain Search Report, Nov. 3, 2011.

* cited by examiner

*Primary Examiner* — Charles Boyer
(74) *Attorney, Agent, or Firm* — Curatolo Sidoti Co., LPA; Joseph G. Curatolo; Salvatore A. Sidoti

(57) ABSTRACT

A rinse-off composition, such as a shampoo, hair conditioner or shower gel, comprising a rinse-off composition base, lactoyl ethanolamine and at least one compound selected from the group consisting of N-(4-cyanomethylphenyl) p-menthanecarboxamide and N-(2-pyridin-2-ylethyl) p-menthanecarboxamide. The compositions provide a pleasant, long-lasting cooling sensation.

18 Claims, 3 Drawing Sheets

0.4% menthol + 1% lactoyl ethanolamine + 0.1% Evercool™ 190

Area under the curve = 108.16

0.4% menthol + 1% lactoyl ethanolamine + 0.2% menthyl pyrrolidone carboxylate

Area under the curve = 48.29

0.4% menthol + 1% lactoyl ethanolamine + 0.5% menthoxypropane 1,2-diol

Area under the curve = 60.92

RINSE-OFF COMPOSITIONS COMPRISING LACTOYL ETHANOLAMINE AND A MENTHANECARBOXAMIDE COMPOUND

CROSS REFERENCE TO RELATED APPLICATIONS

This application is a national stage application of International Application No. PCT/EP2012/064697, filed 26 Jul. 2012, which claims priority from Great Britain Patent Application No. 1112787.5, filed 26 Jul. 2011, and Great Britain Patent Application No. 1209657.4, filed 31 May 2012, from which applications priority is claimed, and which applications are incorporated herein by reference.

This disclosure relates to rinse-off compositions and to materials for use therein.

By "rinse-off composition" is meant a composition that is applied to the exterior of human body and then rinsed off, rather than being allowed to remain. The most common variety of such composition is hair shampoo, but there are other hair-care products, such as conditioners, plus shower gels that are applied to the skin and hair when showering.

Because they are in contact with the skin for a limited time, such products must exert their desired effects quickly. While this is rarely a problem for surfactant-related properties, such as cleaning or hair conditioning, it is a problem when other properties are desired.

One such property is cooling. It has long been known that certain chemical compounds can provide a cooling sensation to the skin and mucous membranes of the body. The original cooling compound was the naturally-occurring menthol, but there have subsequently been found other compounds, some related to menthol, some not at all related, which deliver more powerful cooling effects. Normally the cooling effect is sensed more noticeably on the mucous membranes, where the receptors are closer to the surface. As a result, cooling compounds have a more difficult time being sensed on the skin, and this is accentuated in a rinse-off composition, where the time to exert the desired effect is limited. As a result, rinse-off compositions that provide a pleasant cooling sensation, generally containing menthol, are rare, and the cooling effect is not long-lasting.

In a recent development, described in PCT International publication WO 2008/107137, it was found that the performance of coolants in topically-applied compositions such as cosmetics and toiletries could be enhanced by the addition of certain compounds in addition to known cooling compounds. However, this document said nothing about rinse-off compositions and their problems.

It has now been surprisingly found that a particular combination of cooling compounds and other compounds gives a particularly effective cooling sensation when used in rinse-off products. There is therefore provided a rinse-off composition, comprising a rinse-off composition base, lactoyl ethanolamine and at least one compound selected from the group consisting of N-(4-cyanomethylphenyl) p-menthanecarboxamide and N-(2-pyridin-2-ylethyl) p-menthanecarboxamide.

There is additionally provided a method of providing a pleasant cooling sensation in a rinse-off composition, comprising the incorporation in the composition of an effective proportion of lactoyl ethanolamine and at least one compound selected from the group consisting of N-(4-cyanomethylphenyl) p-menthanecarboxamide and N-(2-pyridin-2-ylethyl) p-menthanecarboxamide.

Figure 1:
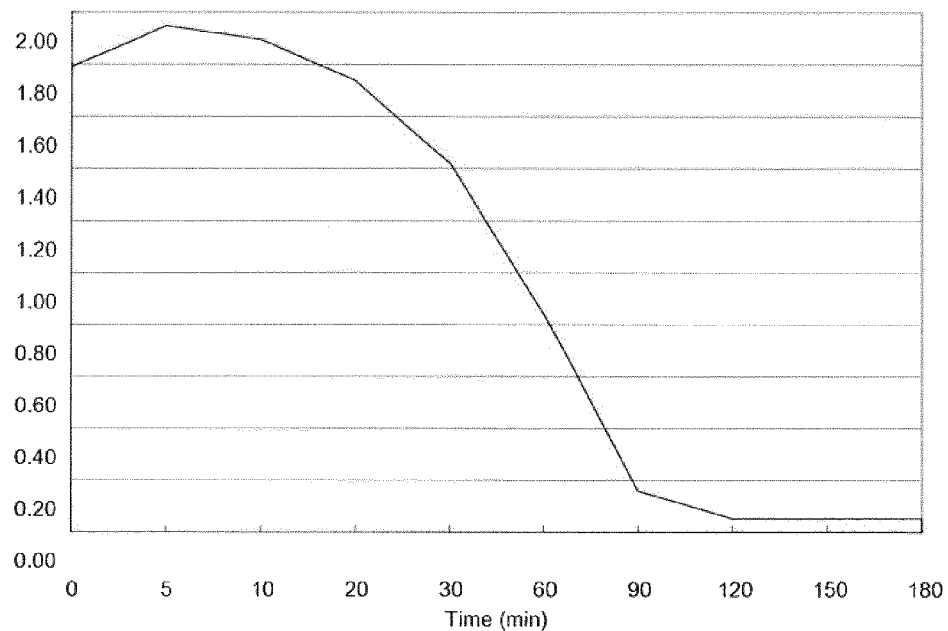
FIG. 1 is a graph indicating the average cooling effects experienced by 10 panellists, plotting the degree of coolness over time for a composition containing N-(2-pyridin-2-ylethyl) p-menthanecarboxamide.

The compounds N-(4-cyanomethylphenyl) p-menthanecarboxamide and N-(2-pyridin-2-ylethyl) p-menthanecarboxamide are known as cooling agents from PCT International publications WO 2005/049553 and WO 2007/019719. They are extremely effective cooling agents for the mucous membranes, but, like other excellent cooling agents, their effectiveness on the skin has proved to be noticeably lower. However, in this particular composition, they are surprisingly effective. In a particular embodiment, both of these compounds are used in a hair-care composition.

Lactoyl ethanolamine is known as an enhancer for cooling agents, for example, from PCT International publication WO 2008/107237. The two cooling agents hereinabove mentioned are mentioned in this publication. However, there is no indication that the particular combination of lactoyl ethanolamine and one or both of these compounds would result in such an effective rinse-off composition.

By "rinse-off composition base" is meant all of the normal ingredients, other than the cooling component hereinabove mentioned, used to formulate such compositions, used in art-recognised proportions. Such ingredients will naturally depend on the nature of the rinse-off composition, but they typically include surfactants, colouring matters, fragrance (including encapsulated fragrance), thickeners and rheology modifiers, conditioning agents, antidandruff actives, UV-block actives, and the like.

To the base, the lactoyl ethanolamine, N-(4-cyanomethylphenyl) p-menthanecarboxamide and/or N-(2-pyridin-2-ylethyl) p-menthanecarboxamide mixture is added. The proportions of the components are (by weight of the total rinse-off composition) from 1-5%, particularly from 1-3%, of lactoyl ethanolamine, and from 0.01-0.1%, particularly from 0.05-0.1%, of either or a combination of N-(4-cyanomethylphenyl) p-menthane-carboxamide and N-(2-pyridin-2-ylethyl) p-menthanecarboxamide. In a particular embodiment, the weight ratio of lactoyl ethanolamine to N-(4-cyanomethylphenyl)-p-menthanecarboxamide and/or N-(2-pyridin-2-ylthyl)-p-menthanecarboxamide is from 5:1 to 20:1, particularly from 7:1 to 15:1, and more particularly from 9:1 to 11:1.

In a further particular embodiment, the mixture is lactoyl ethanolamine and N-(2-pyridin-2-ylthyl)-p-menthanecarboxamide. This is used in a mixture of weight proportions from 90-95%, particularly from 91-93%, lactoyl ethanolamine, and 5-10%, particularly from 7-9%, N-(2-pyridin-2-ylthyl)-p-menthanecarboxamide.

The rinse-off compositions are prepared by standard methods and are used like any other such composition. As well as performing the desired function, the rinse-off compositions provide a pleasant, cooling sensation that is long-lasting, up to 50% longer than a shampoo utilising menthol.

The disclosure is further described with reference to the following example, which describes preferred embodiments, and which is in no way meant to be limiting on the scope of the disclosure.

EXAMPLE 1

(i) Preparation of Shampoo Base

The following materials were combined by mixing the weight proportions of the following ingredients:
- Sodium Laureth-3 Sulfate=14%
- Sodium Lauryl Sulfate=3%
- Cocamidopropylbetaine=4%
- Cocamide MEA=0.8%
- Cetyl Alcohol=0.3%
- Polyquaternium-10=0.2%
- Acrylate Copolymers=2%
- EGDS=2%
- Silicone Emulsion (DC1352—Dow Corning)=4%
- Hydrogenated Polyisobutene=0.5%
- Methylisothiazolinone and Methyl chloroisothiazolinone=0.2%
- Zinc Pyrithione (50%)=1.50%
- Fragrance=0.6%
- Sodium Chloride=0.1-0.2%
- Disodium EDTA=0.2%
- Water=up to 100%

(ii) Preparation of Test Samples

To equal proportions of the shampoo base previously described, the following materials and proportions (by weight of the total composition) were added to give three shampoos.
- (a) Menthol—0.4%
- (b) menthol+lactoyl ethanolamine–0.4%+1%
- (c) menthol+lactoyl ethanolamine+N-(2-pyridin-2-ylethyl) p-menthanecarboxamide*–0.4%+1%+0.1%

\* Evercool™ 190, ex Givaudan

(iii) Testing of Samples

The samples were submitted to a test panel of 10 panelists. The panelists were asked to wash their hair and then record their impressions according to certain criteria. The results are shown in the following table. Apart from overall preference, these are averages of the individual ratings given by the panelists.

| Shampoo sample | (a) | (b) | (c) |
|---|---|---|---|
| Perceived overall cooling effect* | 4.1 | 3.9 | 5 |
| Perceived cooling sensation while washing hair** | 2.4 | 2.2 | 2.5 |
| Perceived cooling sensation while rinsing hair** | 2.7 | 2.55 | 2.8 |
| Perceived cooling sensation after rinse on wet hair** | 2.65 | 2.7 | 2.9 |
| Perceived cooling sensation after drying hair** | 2.6 | 2.55 | 2.9 |
| Perceived length of cooling sensation after drying*** | 2 | 1.75 | 3 |
| Overall preference (no. of testers) | 3 | 1 | 6 |

The ratings explanation is as follows:
*Scale of 1-7, where 1 is very poor and 7 is excellent
**Scale of 1-5, where 1 is much too weak, 5 is much too strong and 3 is optimal
***Scale of 1-5, in which
1 = 1-15 minutes
2 = 16-30 minutes
3 = 31-45 minutes
4 = 46-60 minutes
5 = >60 minutes It can be seen that the composition of this disclosure is rated as superior in every department, and the number of panelists who found it overall superior is considerably higher than those who preferred the other two shampoos combined.

EXAMPLE 2

To samples of the shampoo base of Example 1, the following cooling mixtures were added, the percentages being by weight of the complete composition:

0.4% menthol+1% lactoyl ethanolamine+0.1% Evercool™ 190

0.4% menthol+1% lactoyl ethanolamine+0.2% menthyl pyrrolidone carboxylate*

0.4% menthol+1% lactoyl ethanolamine+0.5% menthoxypropane 1,2-diol**

Figure 2:
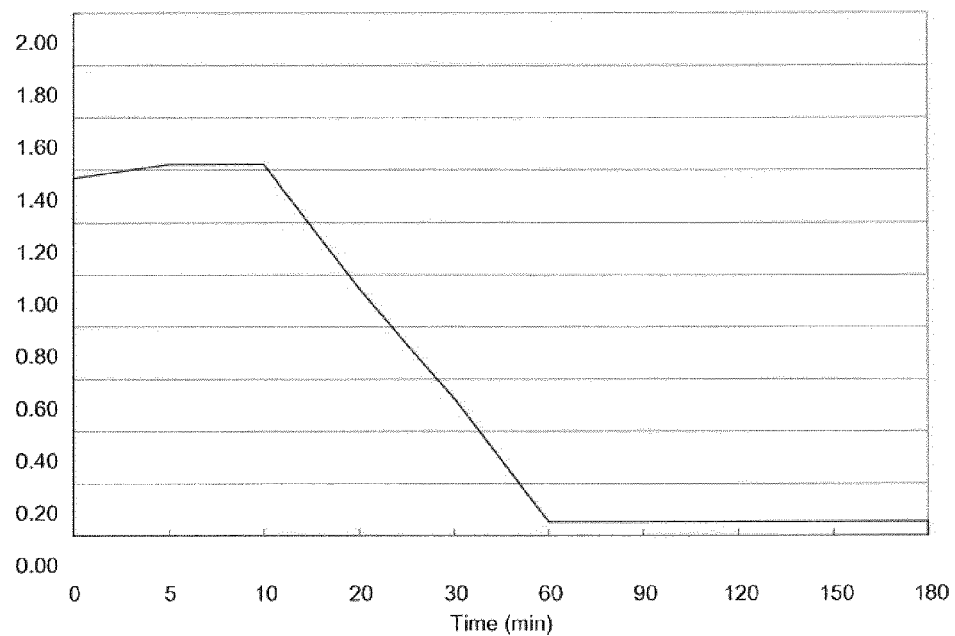
FIG. 2 is a graph indicating the average cooling effects experienced by 10 panellists, plotting the degree of coolness over time for a composition containing the commercial cooling compound menthyl pyrrolidone carboxylate.
Figure 3:
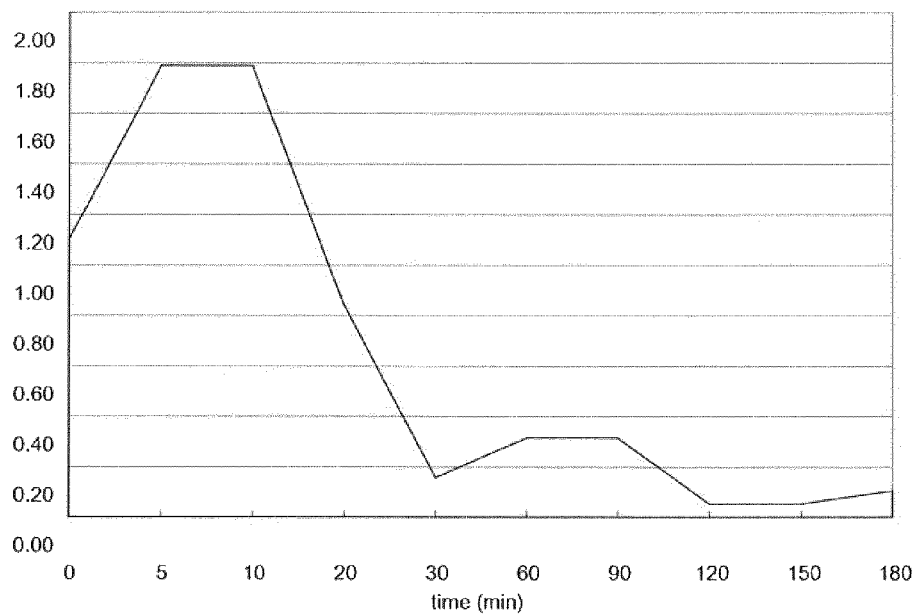
FIG. 3 is a graph indicating the average cooling effects experienced by 10 panellists, plotting the degree of coolness over time for a composition containing the commercial cooling compound menthoxypropane 1,2-diol.

\* Questice™ L ex Givaudan
\*\* Coolant No. 10, ex Takasago 10 panellists used these shampoos to wash their hair and they reported on the degree of coolness experienced over a period of 3 hours, assessment being based on the following scale:
0=no cooling
1=slight degree of cooling
2=cooling
3=strong cooling
4=extremely strong cooling The results were averaged and plotted on the graphs shown in FIGS. 1-3, the degrees of coolness being represented on the vertical axes of the graphs. The areas under the respective curves were indicative of the cooling effects experienced. These areas were calculated and were found to be as follows:
FIG. 1: 108.16
FIG. 2: 48.29
FIG. 3: 60.92

It can be seen that the composition containing the N-(2-pyridin-2-ylethyl) p-menthanecarboxamide is substantially better than the compositions containing one of two commercially-successful cooling compounds.

The invention claimed is:

1. A rinse-off composition, comprising a rinse-off composition base, lactoyl ethanolamine and at least one compound selected from the group consisting of N-(4-cyanomethylphenyl) p-menthanecarboxamide and N-(2-pyridin-2-ylethyl)-p-menthanecarboxamide.

2. The rinse-off composition according to claim 1, in which the compound is N-(2-pyridin-2-ylethyl)-p-menthanecarboxamide.

3. The rinse-off composition according to claim 1, in which the proportions of the components are (by weight of the total rinse-off composition) from 1-5% of lactoyl ethanolamine, and from 0.01-0.1% of at least one of N-(4-cyanomethylphenyl) p-menthane-carboxamide and N-(2-pyridin-2-ylethyl) p-menthanecarboxamide.

4. The rinse-off composition according to claim 1, in which the weight ratio of lactoyl ethanolamine to N-(4-cyanomethylphenyl)-p-menthane carboxamide and/or N-(2-pyridin-2-ylthyl)-p-menthanecarboxamide is from 5:1 to 20:1.

5. The rinse-off composition according to claim 2, in which lactoyl ethanolamine and N-(2-pyridin-2-ylthyl)-p-menthanecarboxamide are in the weight proportion of from 90-95% lactoyl ethanolamine, and 5-10% N-(2-pyridin-2-ylthyl)-p-menthanecarboxamide.

6. A method of providing a pleasant cooling sensation in a rinse-off composition, comprising the incorporation in the composition of an effective proportion of lactoyl ethanolamine and at least one compound selected from the group consisting of N-(4-cyanomethylphenyl) p-menthanecarboxamide and N-(2-pyridin-2-ylethyl) p-menthanecarboxamide.

7. The method according to claim 6, in which the proportions of the components are (by weight of the total rinse-off composition) from 1-5% of lactoyl ethanolamine, and from 0.01-0.1% of at least one of N-(4-cyanomethylphenyl) p-menthane-carboxamide and N-(2-pyridin-2-ylethyl) p-menthanecarboxamide.

8. The method according to claim 6, in which the weight ratio of lactoyl ethanolamine to N-(4-cyanomethylphenyl)-p-menthane carboxamide and/or N-(2-pyridin-2-ylthyl)-p-menthanecarboxamide is from 5:1 to 20:1.

9. The method according to claim 6, in which the compound is N-(2-pyridin-2-ylethyl)-p-menthanecarboxamide.

10. The method according to claim 9, in which in which lactoyl ethanolamine and N-(2-pyridin-2-ylthyl)-p-menthanecarboxamide are in the weight proportion of from 90-95% lactoyl ethanolamine, and 5-10% N-(2-pyridin-2-ylthyl)-p-menthanecarboxamide.

11. The rinse-off composition according to claim 1, in which the proportions of the components are (by weight of the total rinse-off composition) from 1-3% of lactoyl ethanolamine, and from 0.05-0.1% of at least one of N-(4-cyanomethyl phenyl) p-menthane-carboxamide and N-(2-pyridin-2-ylethyl) p-menthane carboxamide.

12. The rinse-off composition according to claim 1, in which the weight ratio of lactoyl ethanolamine to N-(4-cyanomethylphenyl)-p-menthanecarboxamide and/or N-(2-pyridin-2-ylthyl)-p-menthanecarboxamide is from 7:1 to 15:1.

13. The rinse-off composition according to claim 1, in which the weight ratio of lactoyl ethanolamine to N-(4-cyanomethylphenyl)-p-menthanecarboxamide and/or N-(2-pyridin-2-ylthyl)-p-menthanecarboxamide is from 9:1 to 11:1.

14. The rinse-off composition according to claim 2, in which lactoyl ethanolamine and N-(2-pyridin-2-ylthyl)-p-menthanecarboxamide are in the weight proportion of from 91-93% lactoyl ethanolamine, and from 7-9% N-(2-pyridin-2-ylthyl)-p-menthanecarboxamide.

15. The method according to claim 6, in which the proportions of the components are (by weight of the total rinse-off composition) from 1-3% of lactoyl ethanolamine, and from 0.05-0.1% of at least one of N-(4-cyanomethyl phenyl) p-menthane-carboxamide and N-(2-pyridin-2-ylethyl) p-menthane carboxamide.

16. The method according to claim 6, in which in which the weight ratio of lactoyl ethanolamine to N-(4-cyanomethylphenyl)-p-menthanecarboxamide and/or N-(2-pyridin-2-ylthyl)-p-menthanecarboxamide is from 7:1 to 15:1.

17. The method according to claim 6, in which in which the weight ratio of lactoyl ethanolamine to N-(4-cyanomethylphenyl)-p-menthanecarboxamide and/or N-(2-pyridin-2-ylthyl)-p-menthanecarboxamide is from 9:1 to 11:1.

18. The method according to claim 9, in which in which lactoyl ethanolamine and N-(2-pyridin-2-ylthyl)-p-menthanecarboxamide are in the weight proportion of from 91-93% lactoyl ethanolamine, and 7-9% N-(2-pyridin-2-ylthyl)-p-menthanecarboxamide.

* * * * *